United States Patent [19]

Berke et al.

[11] Patent Number: 4,561,445

[45] Date of Patent: Dec. 31, 1985

[54] ELONGATED NEEDLE ELECTRODE AND METHOD OF MAKING SAME

[75] Inventors: Joseph J. Berke, 2063 Long Lake Shore Dr., West Bloomfield, Mich. 48033; Charles T. Michael, Troy, Mich.

[73] Assignee: Joseph J. Berke, West Bloomfield, Mich.

[21] Appl. No.: 498,143

[22] Filed: May 25, 1983

[51] Int. Cl.[4] .............................................. A61B 5/04
[52] U.S. Cl. .................................. 128/642; 604/274; 163/5
[58] Field of Search ............... 128/642, 734, 784, 741, 128/303.18, 329 R, 329 A, 339, 340; 604/239, 272–274; 163/1, 5; D24/24, 25

[56] References Cited

U.S. PATENT DOCUMENTS

| 2,560,162 | 7/1951 | Ferguson | 604/274 |
| 3,308,822 | 3/1967 | DeLuca | 604/274 |
| 3,788,119 | 1/1974 | Arrigo | 604/274 |
| 3,788,320 | 1/1974 | Dye | 604/272 |

OTHER PUBLICATIONS

Pollak, Med. and Biol. Eng., vol. 9, No. 6, p. 658, Nov. 1971.

Primary Examiner—Lee S. Cohen
Attorney, Agent, or Firm—Cullen, Sloman, Cantor, Grauer, Scott & Rutherford

[57] ABSTRACT

A improved needle and method of forming the improved needle from an elongated cylindrical shank. The needle is formed by first cutting or grinding one end of the shank to create a first bevel surface disposed at an angle to the longitudinal axis of the needle. Thereafter as many as five additional bevel surfaces are formed or ground at the end of the shank with each bevel surface removing at least a portion of the peripheral edge of a previously formed bevel surface.

10 Claims, 12 Drawing Figures

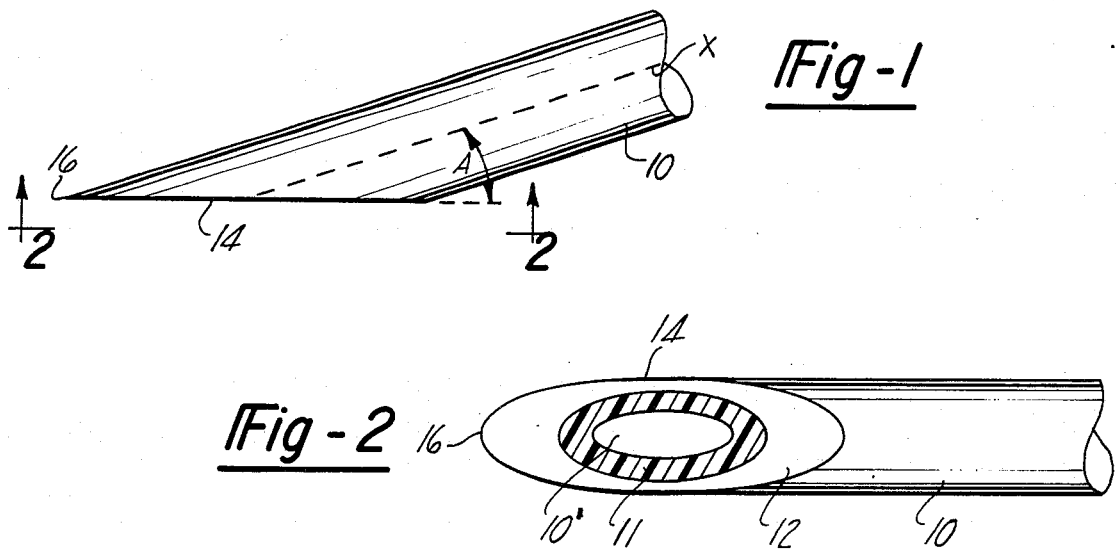
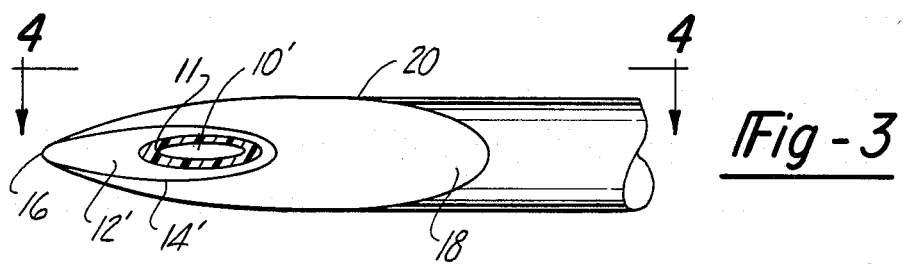
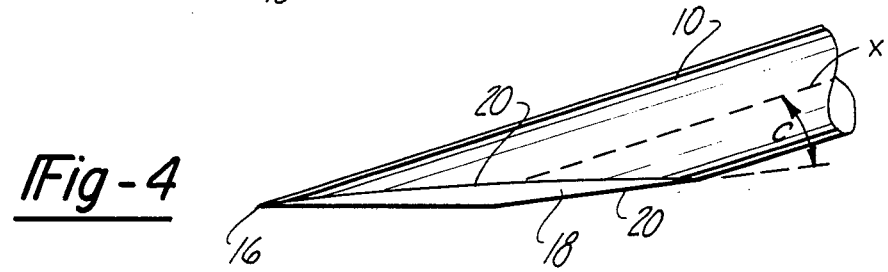
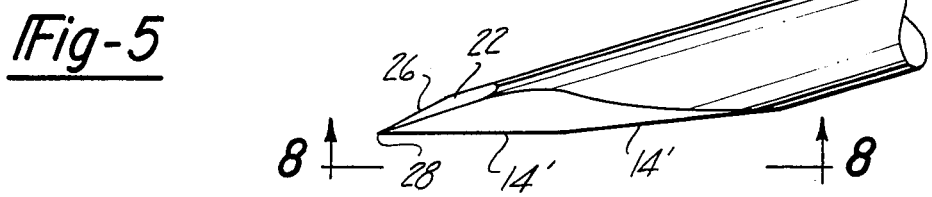

FIG. 2 is a bottom view of the needle electrode of FIG. 1 as seen in the direction of arrows 2—2 of FIG. 1;

FIG. 3 is a bottom view of the needle electrode after a second facet or bevel has been formed therein in accordance with the principles of the present invention;

FIG. 4 is a side elevation view of the needle electrode of FIG. 3 as seen in the direction of arrows 4—4 of FIG. 3;

FIG. 5 is an end view of the needle electrode after formation of the third and fourth facets or bevels in accordance with the principles of the present invention;

FIG. 6 is a side elevation view of the needle electrode of FIG. 5;

FIG. 7 is a plan view of the needle electrode of FIG. 5;

FIG. 8 is a bottom view of the needle electrode of FIG. 6 as seen the direction of arrows 8—8 of FIG. 6;

FIG. 9 is a side elevation view of a needle electrode made in accordance with the principles of the present invention;

FIG. 10 is a bottom view of the needle electrode of the present invention as seen in the direction of arrows 10—10 of FIG. 9;

FIG. 11 is an end view of the needle electrode of the present invention as seen in the direction of arrows 11—11 of FIG. 9, and;

FIG. 12 is a cross-section view of the needle electrode as seen in the direction of arrows 12—12 of FIG. 10.

DETAILED DESCRIPTION OF THE INVENTION

The present invention will now be explained with reference to a metal needle electrode of the type which may be used in electromyography. Specifically, the detailed description of the preferred embodiment of the present invention is explained in the context of an electromyography needle having two coaxially aligned concentric electrodes radially spaced apart by an insulating member. However, it should be understood and appreciated that the present invention may be practiced in the making and/or sharpening of hypodermic needles, cannulas, and needles having more than on inner electrode.

Referring now to the drawings, the improved needle electrode 10 is an elongated cylindrical member of generally circular cross-section. The elongated cylindrical member comprises an internal solid cylinder $10^1$, which functions as the inner electrode, an outer hollow cylinder, which is the outer electrode, and an intermediate hollow cylinder 11 of an electrically insulating material. The three cylinders have a common longitudinal central axis "X". For clarity in the drawings, the inner electrode $10^1$ and the insulating member 11 are omitted from several of the illustrations. To make the needle electrode, a first step is to grind one end of the cylindrical member in a plane which intersects the longitudinal axis at an angle "A" which may be about 15°. The grinding forms a first facet or bevel 12 on the surface of the needle electrode. The intersection of the bevel 12 and the periphery of the cylindrical member 10 defines a first edge 14 which is of elliptical shape in plan view. The leading end of the needle electrode so formed is referred to as the point 16.

The method as heretofore described is well-known and results in the disadvantages previously described.

The next step in making the needle electrode of the present invention is to grind away part of the bevel or facet 12 at the end thereof remote from the point 16, and to remove part of the peripheral edge 14. This second grinding step may be described as a grinding down to the first edge 14 and the resulting configuration is a second bevel 18, the edge of which also is of elliptical configuration in plan view. This second bevel or facet 18 has a peripheral edge 20 defined as the intersection of the extremities of the second bevel with the circumference or periphery of the shank of the needle electrode 10. Since the second bevel 18 is formed by grinding the first edge 14, it may be appreciated that the second grinding step actually reduces the size or area of the first bevel 12, to form a modified first bevel $12^1$. Forming the second bevel also modifies or reduces the first peripheral edge to form a modified first edge $14^1$. Furthermore, although the first bevel 12 was initially a plane which intersected the shank, the reduction in size of the first bevel 12 and the creation of the second bevel 18 places the second bevel 18 intermediate the first bevel 12 and the curved periphery of the needle electrode shank. The second bevel 18 extends from the modified first bevel $12^1$ for a circumferential distance which gradually increases from a minimal amount at the point 16 to a maximum amount at the end of the modified first bevel $12^1$ remote from the point 16. Thus the size of bevel 18 increases as the cross-sectional area of the needle electrode increases. As illustrated in FIG. 4, the second bevel 18 appears to be frustro-conical in nature and when viewed in an elevation view, a plane tangent to the center line of the second bevel 18 would be at angle "C" relative to the longitudinal axis "X" of the needle electrode. Angle "C" is smaller than angle "A".

The next steps in the formation of the needle electrode according to the principles of the present invention is to grind third and fourth bevels, or facets, which are also referred to as first and second back surfaces, to sharpen and to support the leading end of the needle electrode. These first and second back surfaces are symmetrically ground on opposite sides of the longitudinal center line of the needle electrode. The first of these back surfaces 22 is formed by grinding part of the peripheral edge 20 and part of the initial point 16 of the needle electrode. The second of these back surfaces 24 (actually the fourth bevel or facet) is ground on the opposite side of the center line, and removes a portion of the second peripheral edge 20 and a portion of the initial point 16. A generally longitudinal edge 26 is defined as by the intersection of the third and fourth bevel surfaces 22, 24, respectively, and the forward most intersection of the third and fourth bevels, which also intersect with the edge 26, is the point 28 of the finished needle electrode.

Thus, when the third and fourth bevel or facet are ground or formed they each remove a portion of the peripheral edge 20 resulting in a modified peripheral edge $20^1$. The third and fourth bevel surfaces 22, 24 also form part of the periphery of the needle electrode causing not only a sharpening of the point 28 but also providing a more gradual increase in the cutting diameter of the needle electrode so that upon insertion and rotation of the needle electrode there is a more clean cutting and less tearing or stretching of tissue.

With reference to FIGS. 9—12, the forming or grinding operations as heretofore described, when employed with a needle having inner and outer electrodes spaced

ELONGATED NEEDLE ELECTRODE AND METHOD OF MAKING SAME

BACKGROUND OF THE INVENTION

The present invention relates to an improved needle and a method of making the same. More specifically, the present invention relates to needle electrodes of the type used in electromyography.

To facilitate an understanding of the present invention, it is helpful to first consider the terminology as used in this application with respect to needles in general and with respect to needle electrodes. Both needles and needle electrodes are usually formed with an elongated body which may be of circular or oval cross-section. The elongated body is often referred to as the shank. One end of the needle is sharpened, for insertion into the skin, and the leading portion of the needle, i.e. the first part of the needle to penetrate the skin, is referred to as the point. Typically, the shank is tapered (i.e., formed with an angularly disposed face) toward the point and the tapered surface of the shank is referred to as a bevel or facet. The point and bevel of the needle together are collectively referred to as the tip.

Heretofore, the bevel has been formed by grinding a flat plane which intersects the longitudinal axis of the shank at a desired angle. The intersection of the flat plane and the circular shank defines an edge, which, in plan view, is of elliptical configuration.

Hypodermic needles, which are a form of cannulas, have a hollow shank and the formation of the bevel as described actually forms two ellipses (in plan view); the first ellipse at the intersection of the bevel with the exterior surface of the shank and the second ellipse at the intersection of the bevel with the periphery of the hollow interior of the shank. The second ellipse has a greater cross-sectional area than the area of the hollow portion of the shank measured at right angles to the longitudinal axis of the shank and this greater cross-sectional area permits greater fluid flow through the needle thus aiding in dispersion of medications (or in withdrawal of fluids in the case of a cannula).

Needle electrodes, such as the type used in electromyography, typically include a shank which is formed of at least two elongated electrically conductive members or electrodes; the first or outer electrode surrounding the second or inner electrode. The inner and outer electrodes may be coaxially aligned and radially spaced apart with an annular cylinder of insulating material therebetween. If a third conductive electrode is present, the third electrode is usually positioned interiorly of the first or outer electrode and each of the electrodes is electrically insulated from the other electrodes. Needle electrodes as used in electromyography may be monopolar, bipolar, etc., depending upon the number of electrodes and the manner in which the electrodes are connected.

When the bevel of the needle or needle electrode is formed by cutting or grinding the shank at an angle to its longitudinal axis to form the point and the tip, neither the point nor the tip are laterally supported against forces exerted thereagainst during insertion of the needle or needle electrode. The lack of lateral support makes the tip vulnerable to breakage during insertion.

In electromyography, a needle electrode is inserted into a muscle and rotated in four 90° increments. After each 90° rotation, an electrical potential or response is measured. One needle electrode used in electromyography is the model 13L65 manufactured by Disa Electronics Division of Disamatic Inc. The model 13L65 electrode includes a bevel ground at a 15° angle relative to the longitudinal axis of the shank. According to the manufacture, the 13L65 needle electrode should be reground after each 10-20 usages. After regrinding the bevel, the manufacturer recommends smoothing or removing the point with a grinding paper and this removes any burrs. However, this smoothing also blunts the point which adds to patient discomfort when the needle is inserted into the patient.

In addition, when a needle electrode is inserted into a patient and thereafter rotated, the edge (i.e. the intersection of the bevel and the shank) is of a rapidly increasing width in a direction away from the point and the edge does not easily cut tissue because the bevel is substantially flat. The tissue, rather than being easily cut by the rotating edge, is instead torn or stretched resulting in pain being incurred by the patient.

SUMMARY OF THE INVENTION

The present invention is directed to an improved needle and a method of making the same. The method of making the needle may be practiced not only to make needles (or needle electrodes) initially but also to regrind or sharpen them when necessary. The improved needle (and needle electrode) of the present invention has a point and a bevel which are of increased resistance to breakage and which are of substantially increased sharpness for easier and less painful needle insertion. The tip includes a plurality of tapered or beveled surfaces which allow the inserted needle to more cleanly cut tissue during rotation thereby reducing the discomfort of electromyography.

The tip of the needle (or needle electrode) of the present invention is multifaceted and is formed by the intersection of a plurality of bevels. Thus the tip is laterally supported by the beveled surfaces against forces applied from several directions. The peripheral edges of each bevel or facet reduce patient discomfort by increasing the lateral sharpness of the needle electrode. The needle electrode can thereby cut tissue without undue tearing or stretching of the tissue.

In a preferred embodiment, an improved electromyography needle electrode is provided having inner and outer coaxially positioned electrodes. At least one bevel or facet is formed on the exposed end of the electrode. Since the bevel is at an angle to the longitudinal axis of the shank, the sensitivity of the needle electrode is improved by the increased amount of exposed surface area. Thereafter, according to the principles of the present invention, additional beveled surfaces are formed on the exposed end of the electrode to not only increase the amount of exposed surface area but to provide for more smooth cutting of tissue as the needle is rotated.

BRIEF DESCRIPTION OF THE DRAWINGS

The above advantages of the present invention, together with other objects and advantages which may be attained by its use, will become more apparent upon reading the following detailed description of the invention taken in conjunction with the drawings. In the drawings, wherein like reference numerals identify corresponding components:

FIG. 1 is a side elevation view of a needle electrode after a first bevel or facet has been formed at one end thereof;

Figure 7:
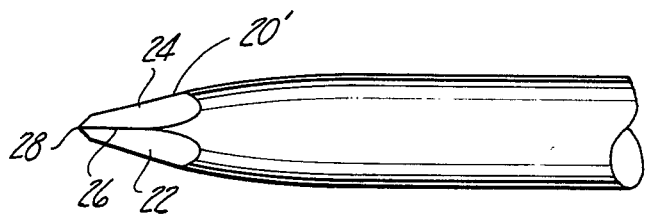
Figure 8:
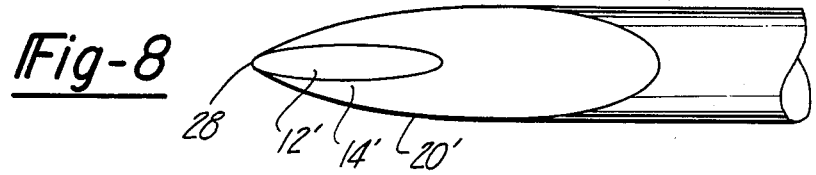
Figure 9:
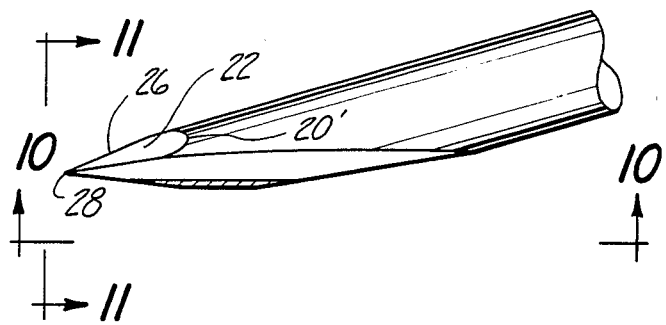
Figure 10:
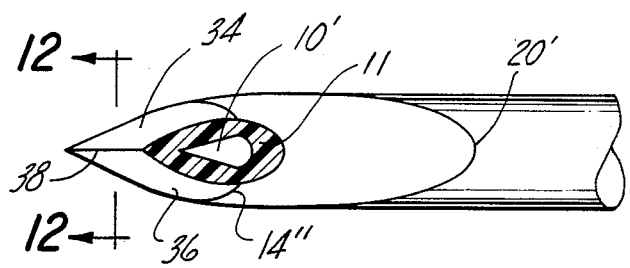
Figure 11:
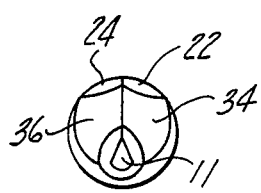
Figure 12:
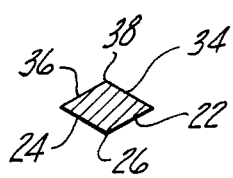

apart by an insulator 11 will typically result in a configuration in which the insulator-11, which is also ground at an angle or bevel, falls within the bevel $12^1$. It should be remembered that the bevel $12^1$ is the final configuration of the first bevel 12 after the subsequent grinding of the second bevel 18. The inner electrode $10^1$ is positioned interiorly of the insulator 11 and the extreme forward tip of the inner electrode $10^1$ is also co-extensive with a portion of the bevel $12^1$. The first or outer electrode, of course, is the needle shank itself.

In the forming or grinding of the needle electrode, it is often desireable to further sharpen the needle electrode and further strengthen the needle electrode tip by the provision of fifth and sixth bevels 34, 36 respectively. While the third and fourth bevels 22, 24 are physically ground on the periphery of the needle electrode opposite to the first bevel 12, the fifth and sixth bevel surfaces 34, 36, which are symmetrical relative to the center line of the needle electrode, are ground over the bevel $12^1$ and at an angle thereto. The bevel $12^1$, of course, is the initial bevel surface 12 which has thereafter been modified by grinding or forming the second bevel 18. The grinding of the fifth and sixth bevels 34, 36 results in a longitudinal edge 38 therebetween, parallel to the edge 26 and 180° around the periphery of the electrode therefrom. When the bevels or facets 34, 36 are formed they further modify the edge $14^1$ resulting in an edge $14^{11}$.

According to the principles of the present invention, the aforementioned sequence of grinding results in a needle electrode which is extremely sharp, extremely rigid and not prone to breakage, and which, because of the numerous cutting edges $14^{11}$, $20^1$, 26 and 38, provides much less painful cutting of tissue when the needle electrode is inserted in a patient and thereafter rotated.

It should be understood and appreciated that the method of making the needle electrode as described may be applied to hypodermic needles and cannulas as well as electromyography needles. When the above technique is applied to a hypodermic needle is should be appreciated that the opening in the hypodermic needle would be advantageously enlarged thus permitting better dispersion of medication. The opening would correspond to the combined insulator 11 and inner electrode $10^1$ of the coaxial needle electrode.

The sharpening or formation of the needle may be accomplished using traditional cutting or grinding tools such as a rotatable cylindrical grinding wheel. It may be further appreciated that consistent grinding from needle to needle may be obtained such as through tape or numerically controlled or computer controlled grinding system with the needle held in a chuck. The edge of the grinding wheel may have a slight concavity for more efficient operation since the present invention includes a needle electrode where the facets are not necessarily flat.

When hypodermic needles or cannulas are being formed, it should be appreciated that the shank can be not only of metal but of a rigid plastic or other material since the principles of the present invention result in a sturdy and sharp needle. Thus materials heretofore not considered for use in hypodermic needles.

Similarly, when electromyography needles are being formed, the metal needle may be initially cast close to the finished shape to reduce the number and/or the extent of the grinding operations. In addition, conductive plastics may be injection molded to the final, desired shape, without any grinding at all and still provide the various bevel surfaces heretofore described.

Accordingly, the configuration of the needle of the present invention may be formed by techniques other than the series of forming steps heretofore described.

The foregoing is a description of the preferred embodiment of the present invention. The invention, however, should be limited only the scope of the following claims.

What is claimed is:

1. An improved needle electrode comprising:
    an elongated insulated body of generally circular cross-section having a first end, a second end and a longitudinal axis;
    an inner conductive electrode in said elongated body extending from the first to the second end of said body;
    a first bevel surface formed at the first end of said body and positioned at an angle relative to the longitudinal axis of the elongated body to form a point at said first end thereby providing an exposed bevel surface area of said inner electrode;
    a first peripheral edge being defined as the intersection of the first bevel with the circumference of said elongated body; and
    a second bevel surface formed at one end of said first bevel surface remote from said point;
    a second peripheral edge defined as the intersection of the second bevel with the circumference of said elongated body;
    said second bevel reducing the exposed surface area of the exposed bevel surface of the inner electrode.

2. The improved needle according to claim 1 wherein said needle first end includes third and fourth bevel surfaces;
    said third and fourth bevel surfaces being symmetrical relative to the longitudinal center line of said elongated body and intersecting with the point of the needle;
    said third and fourth bevel surfaces lying planes which intersect each other to define an edge therebetween.

3. The improved needle according to claim 2 further including fifth and sixth bevel surfaces symmetrical relative to the longitudinal axis of the elongated body and symmetrical relative to the first bevel, and which intersect at the needle point, said fifth and sixth bevel surfaces lying in planes which intersect each other and which define an edge therebetween, said fifth and sixth bevel surfaces further reducing the exposed surface area of the bevel surface of said inner electrode.

4. The improved needle according to claim 3 wherein said elongated body includes an outer conductive electrode surrounding the elongated body and extending from the first end to the second end thereof.

5. The improved needle as defined in claim 3 wherein the leading end of the needle is defined at the intersection of the third, fourth, fifth and sixth bevel surfaces.

6. A method of sharpening a needle of a type having an elongated insulating shank of generally circular cross-section having a first end, a second end, and a longitudinal axis, and an elongated inner conductive electrode extending from the first end to the second end thereof comprising the steps of:
    forming a first bevel surface on the first end of the said shank, said first bevel surface being disposed at an angle relative to the longitudinal axis of the shank, the intersection of said first bevel surface and the cylindrical surface of said shank defining a first edge, said first bevel exposing a first surface area of said inner electrode; and, thereafter forming at least one additional bevel surface at said first end of the shank further reducing the exposed surface area of said inner electrode.

7. The method as defined in claim 6 wherein said step of forming said additional bevel surface includes removing at least a portion of said first edge.

8. The method as defined in claim 6 wherein said step of forming at least one additional bevel includes forming at least three additional bevel surfaces at said one end of the shank, each of which reduces the diameter of said needle by removing at least a portion of the edge formed by a prior bevel surface, at least one of which further reduces the exposed surface area of said inner electrode.

9. The method as defined in claim 6 wherein said step of forming at least one additional bevel surface includes forming at least five additional bevel surfaces at said one end of the shank each of which reduces the diameter of said needle by removing at a portion of the edge formed by a prior bevel surface, at least three of which further reduce the exposed surface area of said inner electrode.

10. A needle made in accordance with the method of claim 6.

* * * * *